(12) United States Patent
Higaki et al.

(10) Patent No.: US 7,267,653 B2
(45) Date of Patent: Sep. 11, 2007

(54) BLOOD COLLECTION NEEDLE

(75) Inventors: Yoshio Higaki, Osaka (JP); Yoshikuni Uchida, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/175,167

(22) Filed: Jul. 7, 2005

(65) Prior Publication Data
US 2006/0009714 A1 Jan. 12, 2006

(30) Foreign Application Priority Data
Jul. 9, 2004 (JP) ............................... 2004-203093

(51) Int. Cl.
*A61B 5/00* (2006.01)
*B65D 81/00* (2006.01)

(52) U.S. Cl. ..................................... 600/576
(58) Field of Classification Search ................ 600/573, 600/575–581; 604/110, 236, 249, 905; 251/149.6
See application file for complete search history.

(56) References Cited

U.S. PATENT DOCUMENTS

| | | | | |
|---|---|---|---|---|
| 3,557,778 A | 1/1971 | Hughes | ...................... | 128/2 |
| 4,106,497 A | 8/1978 | Percarpio | ...................... | 128/2 F |
| 4,307,731 A | 12/1981 | Kaufman | ...................... | 128/766 |
| 4,317,456 A | 3/1982 | Percarpio | ...................... | 128/766 |
| 4,340,068 A | 7/1982 | Kaufman | ...................... | 128/766 |
| 5,222,502 A | 6/1993 | Kurose | ...................... | 128/763 |
| 5,303,713 A | 4/1994 | Kurose | ...................... | 128/763 |
| 5,334,159 A | 8/1994 | Turkel | ...................... | 604/158 |
| 5,527,284 A * | 6/1996 | Ohnemus et al. | ........... | 604/110 |
| 6,050,957 A | 4/2000 | Desch | ...................... | 600/579 |
| 6,991,215 B2 * | 1/2006 | Kiehne | .................... | 251/149.6 |
| 2005/0283093 A1 * | 12/2005 | Conway et al. | ............. | 600/576 |

FOREIGN PATENT DOCUMENTS

| | | |
|---|---|---|
| EP | 633790 B1 * | 5/2000 |
| JP | 53-97289 | 8/1978 |
| JP | 56-143144 A | 11/1981 |
| JP | 57-11661 A | 1/1982 |

* cited by examiner

*Primary Examiner*—Max R Hindenburg
*Assistant Examiner*—Brian Szmal
(74) *Attorney, Agent, or Firm*—Kubovcik & Kobovcik (57) ABSTRACT

A blood collection needle which includes a needle for puncturing a patient's skin; a needle for puncturing a rubber plug which seals a blood collection tube; a hub for securing respective proximal portions of the two needles; a resilient cap fitted to the hub; and a valve member disposed in the internal passage of the hub which allows only blood flow from the needle used to puncture a patient's skin to the needle used to puncture the rubber plug which seals the blood collection tube. The valve member includes a bowl portion disposed so that the opening is faced toward the needle for puncturing the rubber plug and a guiding portion provided on a bottom surface of the bowl portion for causing the valve member to move to a predetermined position which closes the internal passage.

12 Claims, 7 Drawing Sheets

BLOOD COLLECTION NEEDLE

BACKGROUND OF THE INVENTION

The present invention relates to a blood collection needle and, more specifically, to a blood collection needle to be used for collecting blood by puncturing a blood vessel of a subject with one end thereof and inserting the other end into a vacuum blood collection tube so as to communicate the interior of the blood vessel and the interior of the vacuum blood collection tube, thereby collecting blood of an amount corresponding to a negative pressure in the vacuum blood collection tube.

Hitherto, a blood collecting unit which is adapted to be able to draw blood a plurality of times with a single puncture by using a vacuum blood collection tube has been used (for example, see U.S. Pat. Nos. 5,222,502, and 5,303,713, FIG. 5). The blood collecting unit of this type includes a blood collection needle provided with a needle for puncturing a patient's skin, a needle for puncturing a rubber plug of the vacuum blood collection tube, a needle hub which can fix these needles, and a resilient tip mounted to the needle which is to be used for puncturing the vacuum blood collection tube so as to enclose the same; a blood collection tube holder which fixes the blood collection needle and fits onto the vacuum blood collection tube; and the vacuum blood collection tube sealed with the rubber plug.

For collecting blood, the blood collection needle is fixed to the blood collection tube holder first, and the vacuum blood collection tube is fitted to the blood collection tube holder, whereby the needle for puncturing the vacuum blood collection tube is exposed from the resilient tip and hence the vacuum blood collection tube is puntured, thereby starting blood collecting.

When blood collecting is carried out by the blood collecting unit, the internal pressure of the patient's blood vessel is increased by an avascularization member prior to puncture of the needle. However, when the avascularization member is released during blood collecting, the internal pressure of the blood vessel becomes lower than the internal pressure of the blood collection tube, and hence blood in the blood collection tube may flow back into the blood vessel. Since the blood collection tube is generally unsterilized and the interior thereof may be contaminated by bacteria or the blood collection tube may contain chemicals such as blood coagulation agent, damage caused by backflow of the bacteria or the chemicals into the patient with the blood is not desirable.

Such a problem can be solved at least by considering the timing to release the avascularization member. However, since the technique of blood collecting is not consistent, development of a blood collection needle which can prevent backflow of blood from the blood collection tube into the patient's blood vessel without depending on the timing of releasing the avascularization member is desired.

For example, a blood collection needle having a check valve as a mechanism that can prevent backflow of blood has been developed (for example U.S. Pat. No. 3,557,778, JP-A-53-97289, JP-A-57-11661, and JP-A-56-143144). The blood collection needle disclosed in U.S. Pat. No. 3,557,778 includes a ball valve in a needle hub, and when the internal pressure in the patient's blood vessel is lowered to a level lower than the internal pressure in the blood collection tube, the valve moves toward the needle which is inserted in the patient to clog a proximal portion of the needle, thereby preventing backflow of the blood into the patient. The blood collection needle disclosed in JP-A-56-143144 includes a tubular valve disposed in a needle hub, and backflow of blood to the patient can be prevented by the movement of the valve also caused by a pressure difference. On the other hand, the blood collection needles disclosed in JP-A-53-97289 and JP-A-57-11661 include a duckbill valve, which allows only one-way flow of blood, in a needle hub, and when backflow of blood occurs, the valve is closed according to the blood flow, and prevents the blood from flowing back into the blood vessel.

The blood collection needles using the check valve described above can prevent backflow of blood into the patient. However, although the blood collection needles provided with the ball valve or the tubular valve are adapted to cause movement or deformation by the difference between the internal pressure in the blood vessel and the pressure in the blood collection tube, there arises a temporary difference between occurrence of the pressure difference and completion of movement or deformation, and if the pressure difference is very small, the movement or the deformation may not occur, and hence there may be a case where the backflow of blood to the patient cannot be completely prevented. Also, the duckbill valve is expensive, and hence the blood collection needle provided with such a valve is increased in cost even though it is a disposable product.

Accordingly, it is an object of the present invention to provide a blood collection needle which reacts immediately to backflow of blood, is capable of preventing the backflow of blood completely even when the difference between the internal pressure in a blood vessel and the internal pressure in a vacuum blood collection tube is very small, and is kept low in cost.

After having devoted themselves to study, the inventors found that the above-described problems can be solved by a blood collection needle obtained by providing a check valve having a novel shape including a bowl portion which can trap blood which tries to flow backward and a guiding portion which makes the valve move in an adequate direction in a needle hub, and achieved the present invention.

In other words, the present invention is:

(1) a blood collection needle including: a needle tube having an edged distal end for puncturing a patient's skin; a needle tube having an edged distal end for puncturing a rubber plug which seals a blood collection tube; a hub for securing respective proximal portions of the two needle tubes and having an internal passage being capable of bringing the two needle tubes into communication with each other; a resilient cap fitted to the hub so as to embrace, in a liquid-tight manner, the distal end of the needle tube into the rubber plug; and a valve member disposed in the internal passage of the hub which allows only a blood flow from the needle tube puncturing the patient to the needle tube puncturing the rubber plug, characterized in that the valve member includes a bowl portion to be disposed so that an opening is faced toward the needle tube for puncturing the rubber plug and a guiding portion provided on a bottom surface of the bowl portion for causing the valve member to move to a predetermined position which closes the internal passage;

(2) the blood collection needle according to (1), wherein the internal passage of the hub includes a void which accommodates the bowl portion of the valve member and a guiding passage which accommodates the guiding portion of the valve member and can close the internal passage by abutting with an outer peripheral surface of the bowl portion of the valve member;

(3) the blood collection needle according to (2), wherein a portion of the guiding passage of the hub which abuts the outer peripheral surface of the bowl portion of the valve member is formed with an abutment surface having a shape corresponding to the outer peripheral surface of the bowl portion;

(4) the blood collection needle according to any one of (1) to (3), wherein the bowl portion of the valve member has a semi-spherical shape;

(5) the blood collection needle according to any one of (1) to (3), wherein the bowl portion of the valve member has a conical shape;

(6) the blood collection needle according to any one of (1) to (5), wherein the guiding portion of the valve member has a solid column shape;

(7) the blood collection needle according to any one of (1) to (5), wherein the guiding portion of the valve member has a solid conical shape;

(8) the blood collection needle according to (6) or (7), wherein the guiding portion is hollow and communicates with the opening of the bowl portion through the bottom surface of the bowl portion;

(9) the blood collection needle according to any one of (1) to (8), wherein the hub includes a vent path for allowing the internal passage and an outer atmosphere to communicate with each other, and an air permeable/blood impermeable filter fixed within the vent path in a liquid-tight manner;

(10) the blood collection needle according to any one of (1) to (9), further including a spring member which urges the valve member in a direction to close the internal passage, the spring member being disposed in the void of the hub; and (11) the blood collection needle according to (10), wherein the spring member is clamped between the bowl portion of the valve member and a wall surface on the side of the needle tube for puncturing the rubber plug.

ADVANTAGE OF THE INVENTION

According to the blood collection needle of the present invention, backflow of blood from inside the blood collection tube to the blood vessel can be prevented completely irrespective of the technique of blood collecting, that is, the timing of releasing the avascularization member. The check valve employed in the blood collection needle according to the present invention can be maintained low in cost in comparison with the duckbill valve, and can address the backflow of blood much quicker than the conventional check valve.

DESCRIPTION OF THE DRAWINGS

Hereinafter, referring now to the drawings, preferred embodiments of the present invention will be described. However, the invention is not limited thereto.

DETAILED DESCRIPTION OF THE INVENTION

A blood collection needle 1 according to the present invention includes two needle tubes (or cannulae) 21 and 22 having sharp distal ends, and a hub 3 for securing proximal ends of the needle tubes 21 and 22, a resilient cap 4 fitted so as to surround the needle tube 22, and a valve member 5 disposed in the hub 3.

The needle tubes 21 and 22 of the present invention are hollow tubes, and distal ends 211 and 221 thereof are formed with sharp cutting edges. The distal end 211 is for puncturing a blood vessel via a patient's skin, and the distal end 221 is for puncturing a rubber plug which seals a vacuum blood collection tube. The cutting edge thereof includes at least one inclined cutting surface (bevel) for reducing resistance of puncture. For the needle tubes 21 and 22, a metal material such as stainless steel, aluminum, titanium or an alloy thereof is preferably used.

Figure 1:
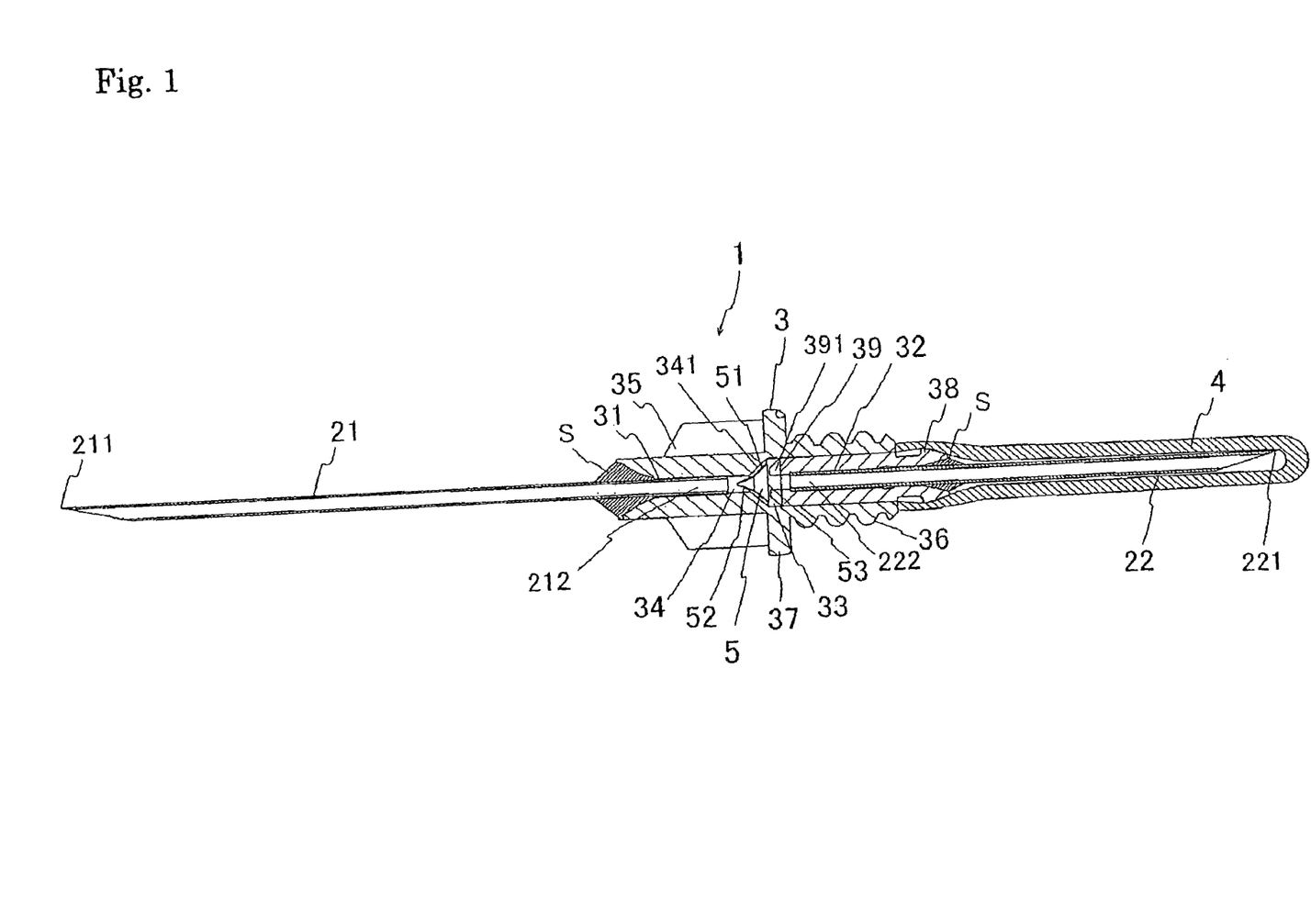
FIG. 1 is a vertical cross-sectional view showing an example of a blood collection needle of the present invention.

The needle tubes 21 and 22 are secured to the hub 3 at the proximal portions 212 and 222 thereof. The hub 3 is a hollow tubular member including internal passages, more specifically, including needle tube holding portions 31 and 32 for inserting the proximal portion 212 of the needle tube 21 and the proximal portion 222 of the needle tube 22, and an internal passage having a void 33 where the later-described valve member is disposed, and a guiding passage 34. The needle tube holding portions 31 and 32 have an inner diameter slightly larger than an outer diameter of the needle tube so that the needle tubes 21 and 22 can be inserted, and the needle tubes 21 and 22 are secured hermetically by, for example, an adhesive agent S after having been inserted into the needle tube holding portions 31 and 32. As the adhesive agent S, epoxy cure agent or UV cure adhesive agent is preferably used. The adhesive agent S may be used so as to fill part of a gap between the hub 3 and the needle tubes 21 and 22 as shown in FIG. 1. The needle tubes 21 and 22 may be secured to the hub 3 coaxially or in parallel, and the positions and the shapes of the needle tube holding portions 31 and 32 may be changed as needed depending on the arrangement of the needle tubes 21 and 22.

The hub 3 of the blood collection needle of the present invention may be provided with a rib 35 on an outer peripheral surface on the side for puncturing the patient. The rib 35 engages a needle cap (not shown) for preventing rotation of the blood collection needle 1 in the needle cap. It is preferable to provide two or more ribs 35 around the entire circumference of the hub 3 at regular intervals.

The hub 3 is formed with a threaded portion 36 on an outer peripheral surface on the side for puncturing the rubber plug, so that a mouth of a blood collection tube holder (not shown) which can fit and hold the vacuum blood collection tube can be screwed on the threaded portion 36. A flange 37 may be formed next to the threaded portion 36 on the side for puncturing the patient so as to limit screwing of the blood collection tube holder by coming into abutment with the mouth of the blood collection tube holder.

The hub 3 may also be formed with an engaging portion 38 with which the later-described resilient cap 4 can be engaged hermetically and inseparably next to the threaded portion 36 on the side for puncturing the rubber plug.

The hub 3 of the blood collection needle of the present invention is molded by known molding techniques such as injection molding with polypropylene, polyethylene, polystyrene, polyethylene terephthalate, polymethylpentene, polycarbonate, polyacrylonitrile, or ABS resin as a material.

Figure 2:
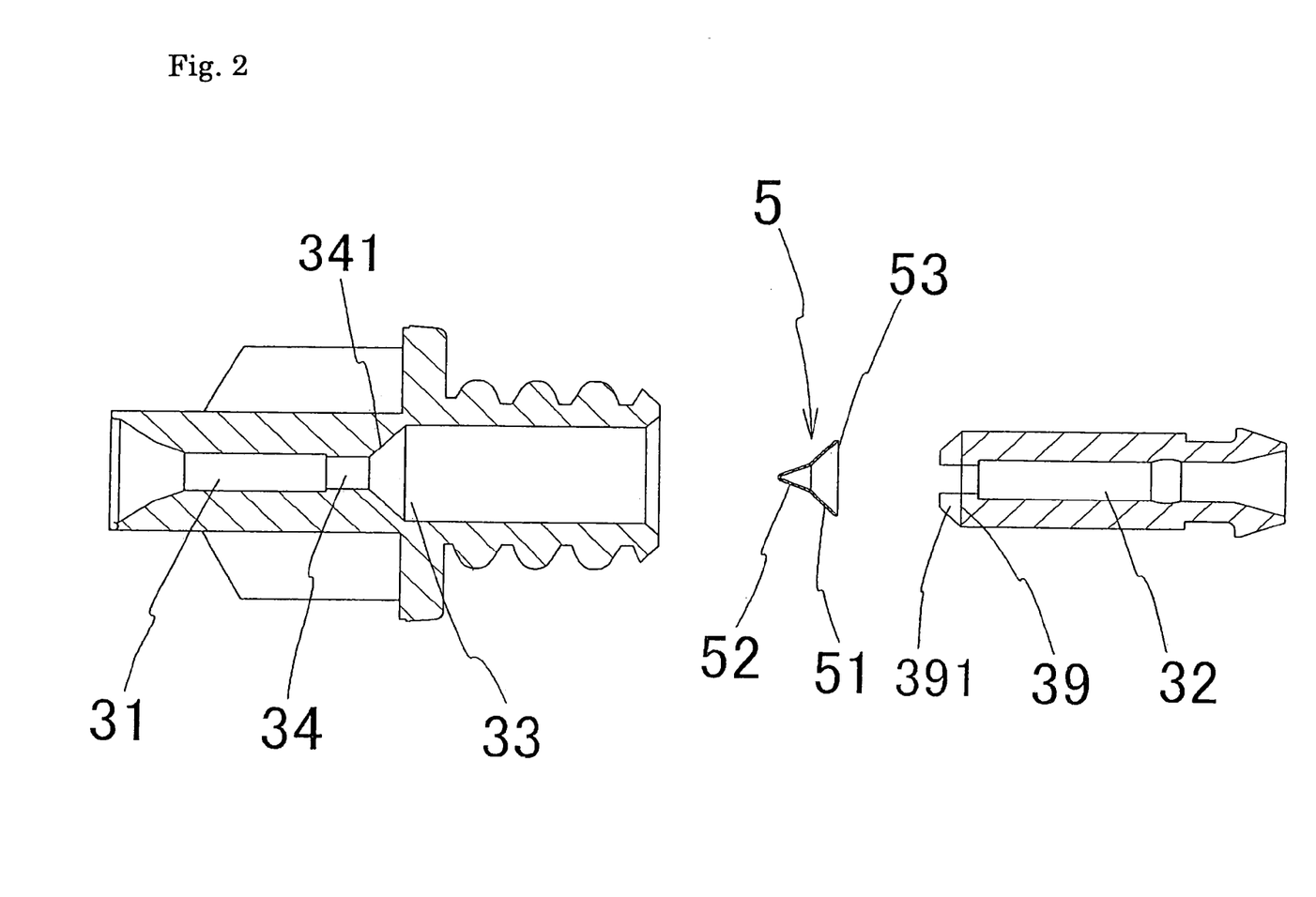
FIG. 2 is an enlarged cross-sectional view showing a hub portion of the blood collection needle of FIG. 1 shown in an exploded state.
Figure 3:
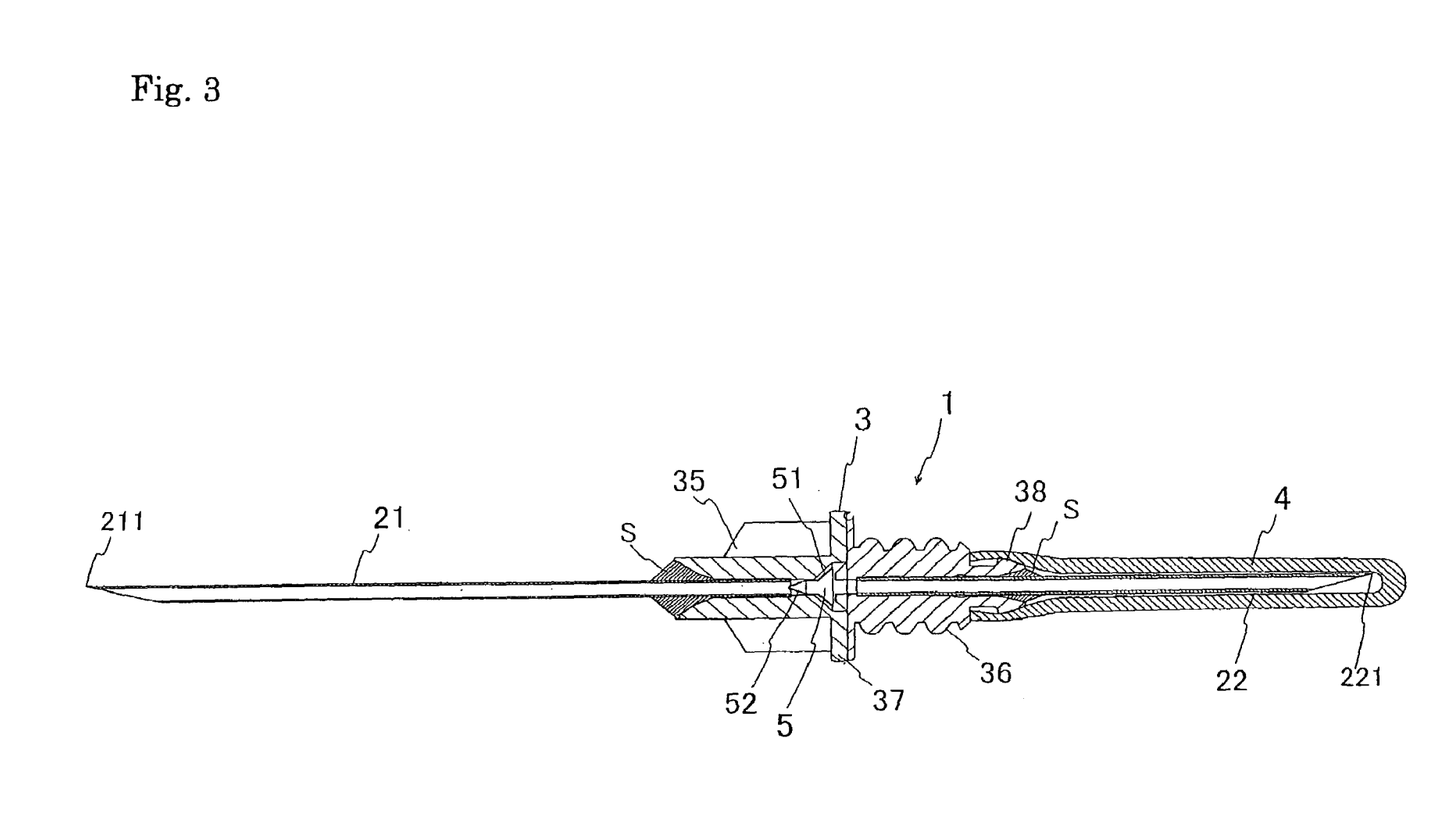
FIG. 3 is a vertical cross-sectional view showing another example of a check valve of the blood collection needle of the present invention.

Since the valve member 5, described later, is disposed in the internal passage, the hub 3 is preferably formed from a plurality of separately molded parts as shown in FIG. 2, which are integrated by welding or adhesion after the valve member 5 is disposed. When molding separate parts of the hub 3, a method of forming an outer member and an inner member separately as shown in FIG. 2 or a method of forming a front end portion and a rear end portion as shown in FIG. 3 may be employed. However, the way of separating the hub is not limited as long as it can be separated into parts for facilitating arrangement of the valve member 5.

The resilient cap 4 to be engaged with the engaging portion 38 of the hub 3 has a bottom cylindrical shape, and has a size sufficient for accommodating the distal end 221 of the needle tube 22. Materials for the resilient cap 4 may be natural rubber, synthetic rubber such as isoprene rubber or silicon rubber, and elastomers. The resilient cap 4 may be at least partly transparent or semi-transparent as needed similar to the hub 3.

The valve member 5 is disposed in the void 33 and the guiding passage 34 formed in the hub 3. The valve member 5 is for allowing only blood flow from the patient's blood vessel to the vacuum blood collection tube during blood collecting and for preventing blood drawn into the vacuum blood collection tube from flowing back to the patient's blood vessel through the blood collection needle 1.

Figure 5:
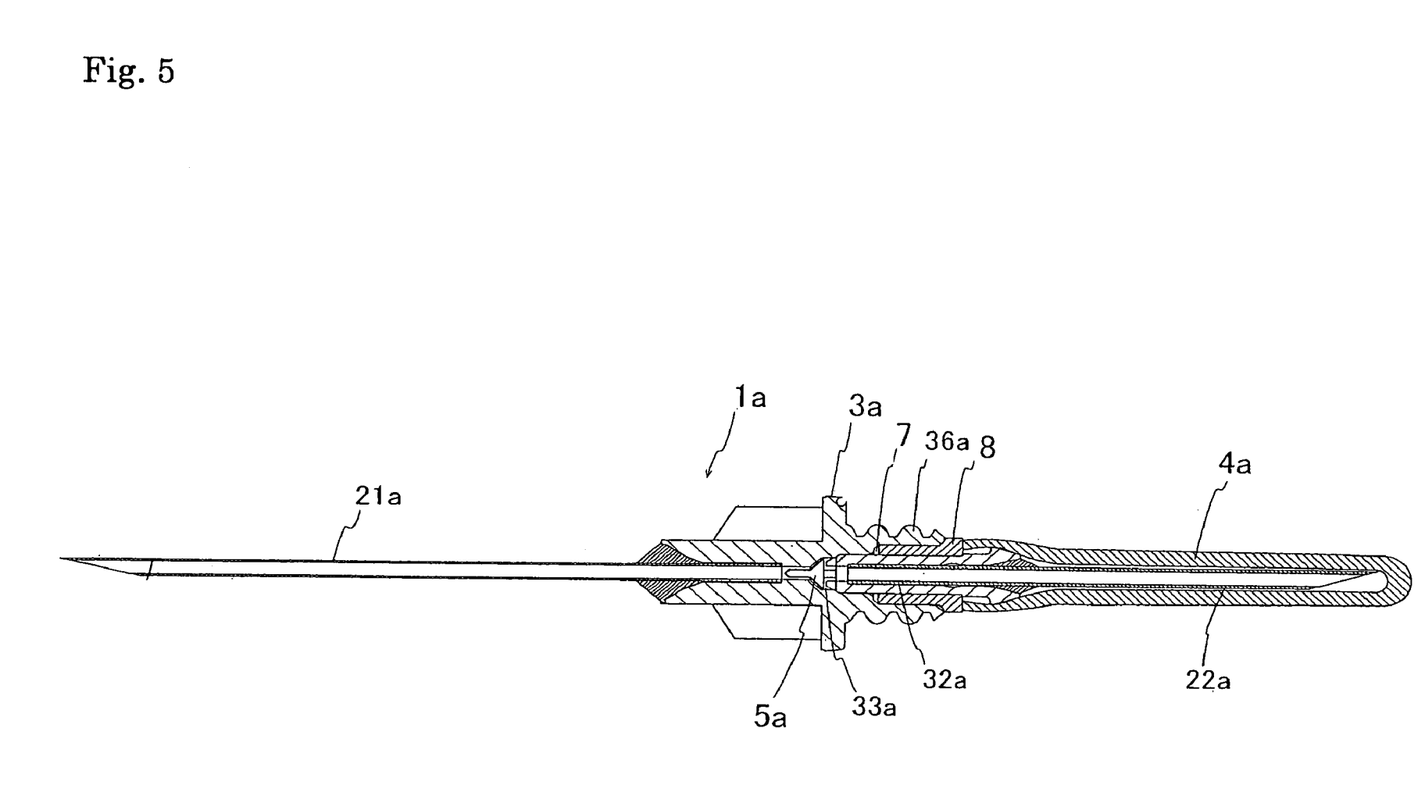
FIG. 5 is a vertical cross-sectional view showing an example of the blood collection needle according to the present invention having a flashback mechanism.

The valve member 5 in the present invention includes a bowl portion 51 and a guiding portion 52 provided on the bottom surface of the bowl portion 51, and is disposed so that an opening 53 of the bowl portion 51 faces toward the proximal portion 222 of the needle tube 22 to be used to puncture the rubber plug. The shape of the bowl portion 51 may be any shape which forms a bowl including a bottom surface and a wall surface so that blood flowing through the opening can be received, such as a frustoconical shape as shown in FIG. 1, semi-spherical shape, column shape, and rectangular column shape. The shape of the guiding portion 52 may be solid cone or column shape as shown in FIG. 1, the combination of a column and a cone as shown in FIG. 3 and FIG. 5, or a rectangular column shape, and is preferably one having an outer diameter smaller than that of the bowl portion 51. The guiding portion 52 may be hollow, and in this case, preferably, the hollow interior is in communication with the opening 53 of the bowl portion 51 through the bottom surface of the bowl portion 51. In other words, when the interior of the guiding portion 52 is hollow, blood flowing through the opening 53 of the bowl portion 51 flows also into the interior of the guiding portion 52.

Material constituting the valve member 5 includes stainless steel, polypropylene, polycarbonate, polyethylene, ABS resin, and so on. A method of molding the valve member 5 includes press molding, injection molding, and so on. The valve member 5 in the present invention may be molded entirely by these molding methods or may be formed separately as a bowl portion 51 and a guiding portion 52 and then integrated by adhesion, bonding, welding, molded-in, or the like.

The valve member 5 is preferably designed in such a manner that the outer diameter of the opening 53 of the bowl portion 51 is larger than the inner diameter of the proximal portion 222 of the needle tube 22 to be used to puncture the rubber plug.

The bowl portion 51 of the valve member 5 is accommodated in the void 33 of the hub 3, and the guiding portion 52 of the valve member 5 is stored in the guiding passage 34 of the hub 3. Therefore, the void 33 and the guiding passage 34 are in communication and the void 33 and the needle tube holding portion 32, and the guiding passage 34 and the needle tube holding portion 31 are also in communication.

Preferably, the void 33 and the guiding passage 34 have a size and shape sufficient for accommodating the bowl portion 51 and the guiding portion 52 of the valve member 5 respectively, and provide a gap for ensuring a sufficient flow rate of blood flowing from the needle tube 21 which punctures the patient's blood vessel during blood collecting to the needle tube 22 which punctures the rubber plug used to seal the vacuum blood collection tube. The void 33 preferably has a column shape or a shape corresponding to the outer peripheral surface of the bowl portion 51, and the guiding passage 34 preferably has a column shape or a shape corresponding to the outer peripheral surface of the guiding portion 52.

When the diameter of the void 33 is larger than the diameter of the needle tube holding portion 32 as shown in FIG. 1, a wall surface 39 is formed at a boundary portion between the void 33 and the needle tube holding portion 32. When blood flows from the patient's blood vessel to the vacuum blood collection tube during blood collecting, the valve portion 5 of the present invention is pressed toward the needle tube 22 of the internal passage of the hub 3 due to the blood flow flowing from the needle tube 21 to the needle tube 22, and hence the opening 53 of the bowl portion 51 abuts against the wall surface 39 of the void 33.

The wall surface 39 may be provided with a rib 391 which projects inwardly of the void 33. During blood collecting, the blood flowing from the needle tube 21 to the guiding passage 34 passes through a gap between the guiding portion 52 and the guiding passage 34, and a gap between the bowl portion 51 and the void 33, and then passes through the needle tube 22 and flows out into the vacuum blood collection tube. Since a gap is defined between the end of the opening 53 and the wall surface 39 by the rib 391, the blood flow is prevented from being blocked due to abutment between the end of the opening 53 of the bowl portion 51 and the wall surface 39. More preferably, a plurality of ribs 391 are provided on the wall surface 39 at regular intervals so as to achieve uniform abutment with the end of the opening 53. When the diameter of the void 33 is smaller than the diameter of the needle tube holding portion 32 and hence the wall surface 39 is not defined, the ribs are provided so as to project inward from the inner peripheral surface of the void 33 on the needle tube 22 side with respect to the bowl portion 51 of the valve member 5.

When the internal pressure in the patient's blood vessel is lowered to a level lower than the internal pressure in the vacuum blood collection tube during blood collecting, the blood in the vacuum blood collection tube tries to flow back through the needle 22 into the internal passage of the hub 3, and then to the patient's blood vessel. However, with the blood collection needle 1 of the present invention, when the blood flowing back through the needle tube 22 is flowed into the void 33, it flows into the interior of the bowl portion 51 and presses the valve member 5 toward the needle tube 21 of the internal passage of the hub 3. Accordingly, the outer peripheral surface of the bowl portion 51 comes into abutment with the guiding passage 34. Since this abutment provides a liquid-tight seal due to the pressure of the blood which flows backward, the blood flowed into the void 33 is prevented from flowing into the guiding passage 34 and the needle tube 21.

Since the valve member 5 of the present invention includes the bowl shaped bowl portion 51 which receives the blood flowing backward, it can close the internal passage of the hub 3 immediately upon occurrence of backflow of the blood. In addition, since the valve member 5 has the guiding portion 52 to be accommodated in the guiding passage 34 of the hub 3, the valve member 5 can be moved quickly toward the needle tube 21 without inclining or rotating the valve member 5 when the blood is flowed backward, and abutment between the outer peripheral surface of the bowl portion 51 and the guiding passage 34 is ensured.

The portion of the guiding passage 34 where the outer peripheral surface of the bowl portion 51 comes into abutment may be formed with an abutment surface 341 having a shape corresponding to the outer peripheral surface of the bowl portion 51. In other words, it is preferable to form the abutment surface 341 having a tapered shape like the outer peripheral surface of the bowl portion 51 when the bowl portion 51 has a conical shape as shown in FIG. 1, and to form the abutment surface 341 notched into a semi-spherical shape like the outer peripheral surface of the bowl portion when, for example, the bowl portion 51 has a semi-spherical shape.

Figure 4:
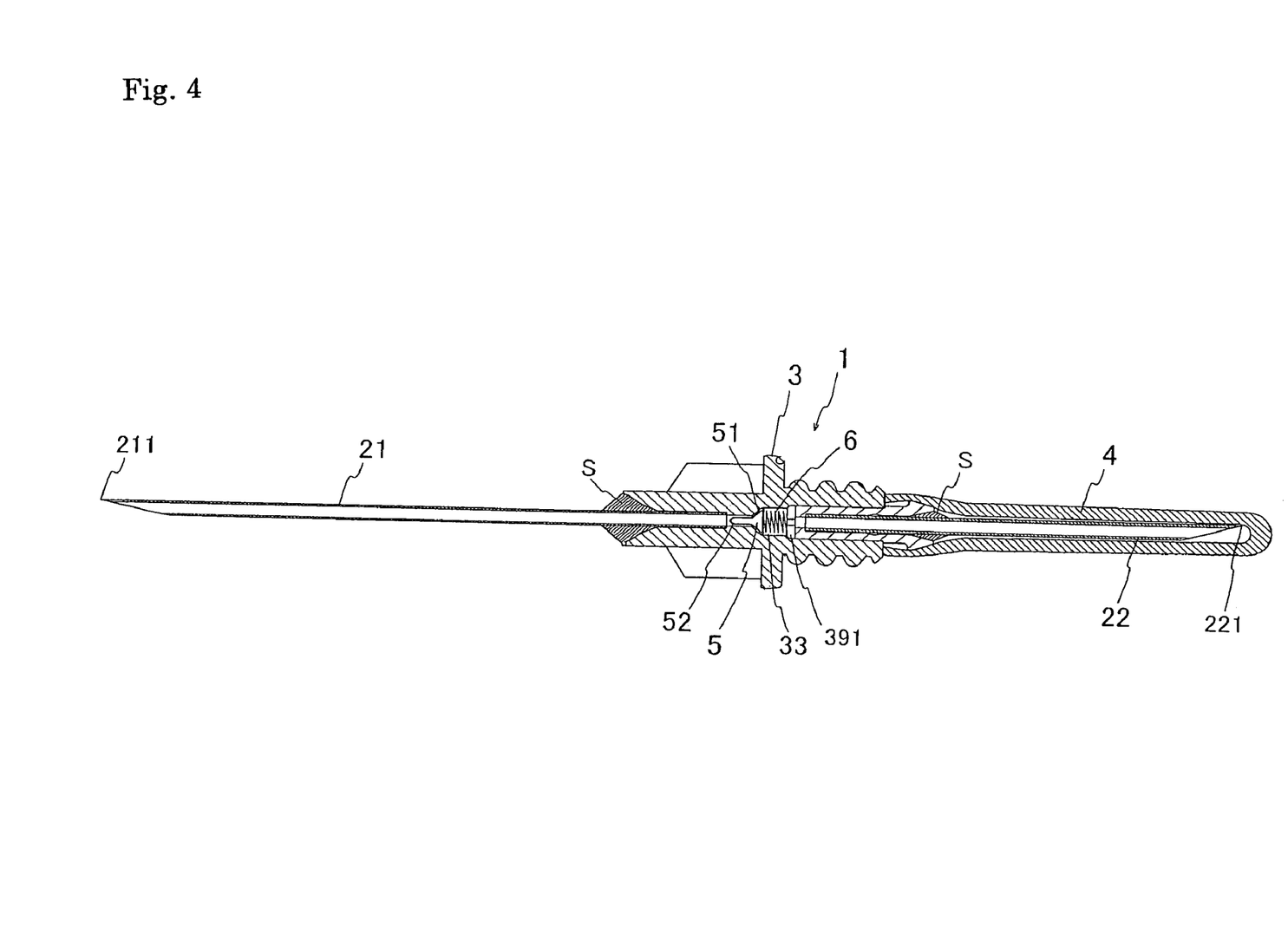
FIG. 4 is a vertical cross-sectional view showing an example of the blood collection needle of the present invention having a spring member.

The blood collection needle 1 according to the present invention may further include a spring member 6 as shown in FIG. 4 as an urging member. The spring member 6 is a spring formed of synthetic resin such as stainless steel, polypropylene, polycarbonate, ABS resin, polyethylene, polyethersulfone, and is clamped between the opening 53 of the bowl portion 51 of the valve member 51 and the wall surface 39 at the boundary portion between the void 33 and the needle tube holding portion 32 in the void 33 of the hub 3. Therefore, preferably, the end of the spring member 6 on the bowl portion 51 side has a diameter larger than the opening 53 of the bowl portion 51, or is fixed to the opening 53. The end of the spring member on the wall surface 39 side can be fixed to the wall surface 39 or the rib 391 as needed.

The spring member 6 is disposed in the void 33 of the hub 3 in a state of being compressed so as to be capable of urging the valve member 5 in the direction of closing the internal passage, that is, toward the needle tube 21. Therefore, by adjusting the urging force of the spring member 6, even when the difference between the internal pressure of the patient's blood vessel and the internal pressure of the vacuum blood collection tube is very small, the valve member 5 is moved toward the needle tube 21 to close the internal passage, thereby reliably preventing backflow of blood. The urging member is not limited to the spring member 6 as long as it can urge the valve member 5, and a resilient member such as a plate-shaped elastomer can also be used.

The blood collection needle 1 according to the present invention may be a blood collection needle 1a having a flashback mechanism as shown in FIG. 5. The blood collection needle 1a has substantially the same components as those of the blood collection needle 1 shown in FIG. 1, and the operation of valve member 5a is the same. The difference between the blood collection needle 1 and the blood collection needle 1a is in that hub 3a has a vent path 7 for communicating the internal passage with the outer atmosphere, in that an air permeable/blood impermeable filter 8 is fixed within the vent path in a liquid-tight manner, and in that the hub 3 is at least partly transparent or semi-transparent so as to enable inspection from the outside of blood flowing into the hub 3.

In the blood collection needle 1a, when a needle tube 21a punctures a blood vessel via a patient's skin, air in the needle tube 21a and air in the internal passage of the hub 3a is released from the vent path 7 through the air permeable/blood impermeable filter 8 toward the outside, and hence blood flows into the needle tube 21a and fills the internal passage of the hub 3a and the vent path 7, and is blocked by the air permeable/blood impermeable filter 8. By visually inspecting the blood from the outside of the blood collection needle 1a through the transparent or semi-transparent portion of the hub 3, the flashback can be confirmed.

The vent path 7 of the blood collection needle 1a may be formed from void 33a to a portion between a threaded portion 36a of the hub 3 and a resilient cap 4a as shown in FIG. 5. However, it may be formed so as to extend from the interior of the resilient cap 4a through the interior of the hub 3a and open at the outer periphery of the hub 3a, or so as to use a needle tube holding portion 32a of the hub 3a as a part of the vent path 7.

Figure 6:
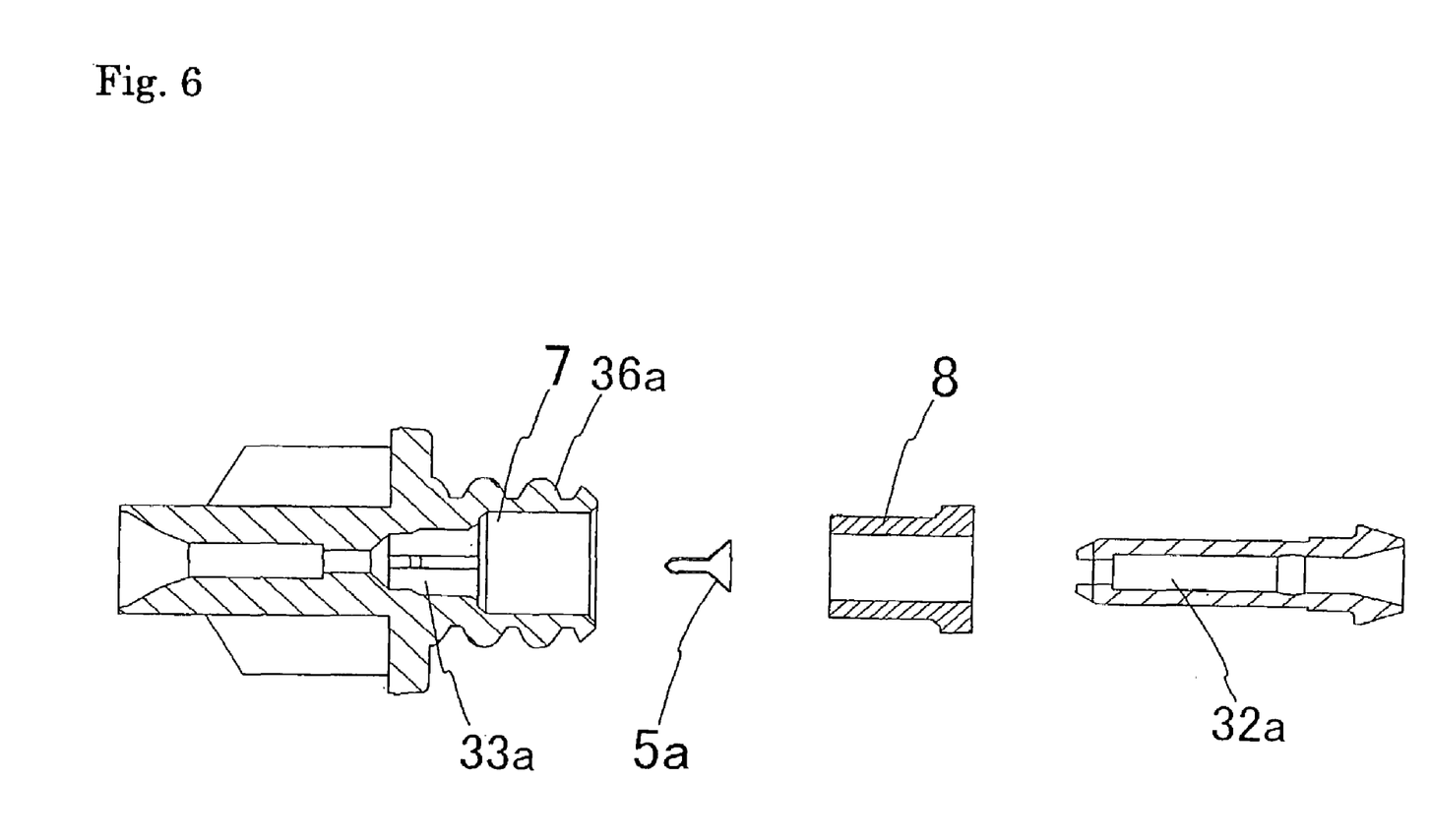
FIG. 6 is an enlarged cross-sectional view of the hub portion of the blood collection needle of FIG. 5 shown in an exploded state.
Figure 7:
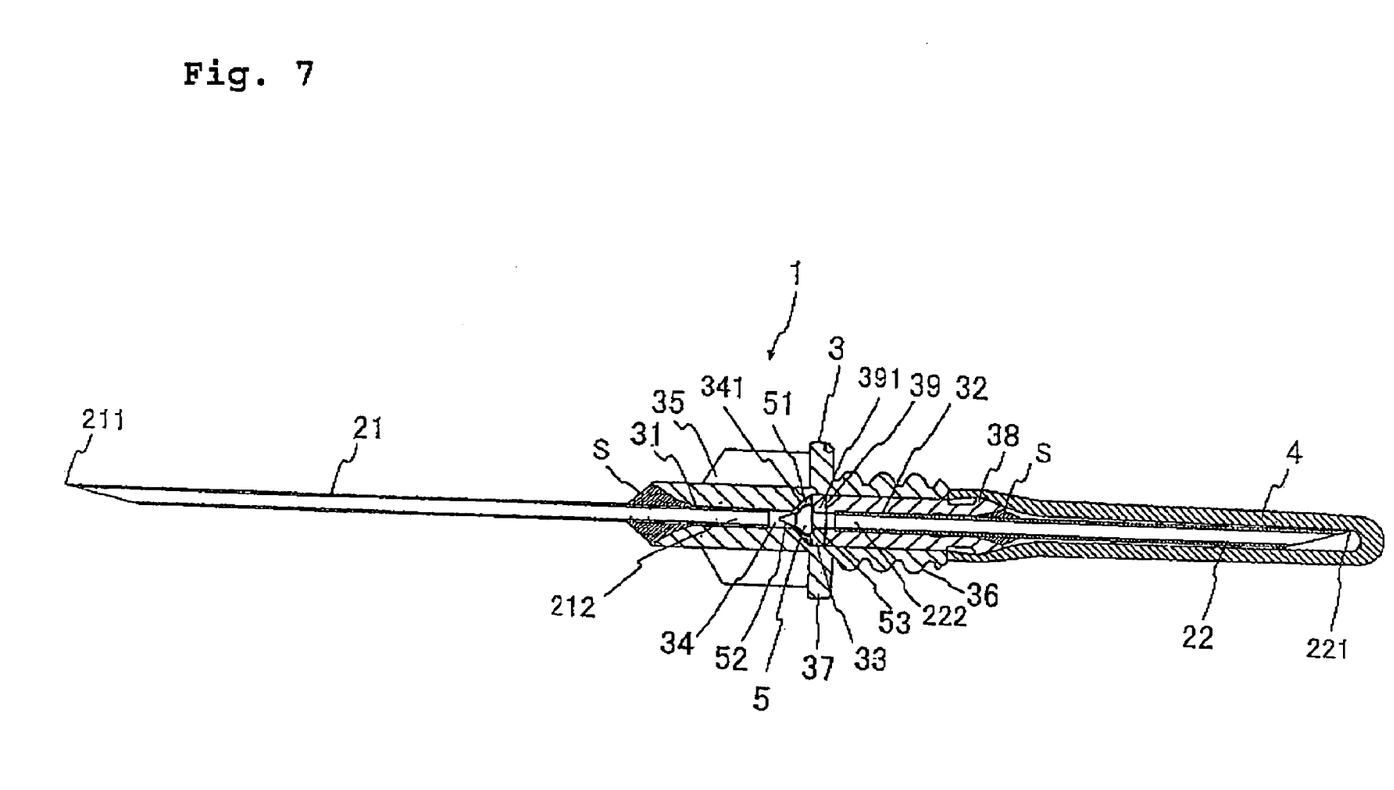
FIG. 7 is a vertical cross-sectional view showing another example of the blood collection needle of the present invention.

Also, the air permeable/blood impermeable filter 8 is not specifically limited as long as it has small holes that allow air to pass and that block liquid and includes a membrane filter or a sintered filter. However, it is a preferably a sintered body formed of polyethylene, polypropylene, polymethylmethacrylate, or polystyrene, or the like, and more preferably, is one having a water absorbing polymer which clogs the small holes of the sintered body by swelling when it comes into contact with blood. As the water absorbing polymer, there is starch and acrylate, and its percentage content is preferably 1 to 30% with respect to the entire weight of the sintered filter. More preferably, the filter 8 has a cylindrical shape as shown in FIG. 6 as long as it can be disposed together with the check valve 5a within the internal passage of the hub 3a as shown in FIG. 5.

This application claims priority of Japanese Patent Application No. 2004-203093, filed Jul. 9, 2004, which is incorporated herein by reference.

What is claimed is:

1. A blood collection needle comprising: a needle tube having a distal end for puncturing a patient's skin; a needle tube having a distal end for puncturing a rubber plug which seals a blood collection tube; a hub for securing respective proximal portions of the two needle tubes and having an internal passage being capable of bringing the two needle tubes into communication with each other; a resilient cap fitted to the hub in a liquid-tight manner so as to enclose the distal end of the needle tube for puncturing the rubber plug; and a valve member disposed in the internal passage of the hub which allows only a blood flow from the needle tube for puncturing the patient to the needle tube for puncturing the rubber plug, wherein the valve member includes (1) a bowl portion having a bottom, a wall and an opening opposite the bottom and disposed so that an opening of the bowl portion faces the needle tube for puncturing the rubber plug and (2) a guiding portion provided on a bottom surface of the bowl portion for causing the valve member to move to a predetermined position in the internal passage which closes the internal passage.

2. The blood collection needle according to claim 1, wherein the internal passage of the hub includes a void which accommodates the bowl portion of the valve member and a guiding passage which accommodates the guiding portion of the valve member and can close The internal passage by abutting with an outer peripheral surface of the bowl portion of the valve member.

3. The blood collection needle according to claim 2, wherein a portion of the guiding passage of the hub which abuts with the outer peripheral surface of the bowl portion of the valve member is formed with an abutment surface having a shape corresponding to the outer peripheral surface of the bowl portion.

4. The blood collection needle according to claim 1, wherein the bowl portion of the valve member has a semispherical shape.

5. The blood collection needle according to claim 1, wherein the bowl portion of the valve member has a frustoconical shape.

6. The blood collection needle according to claim 1, wherein the guiding portion of the valve member has a solid column shape.

7. The blood collection needle according to claim 1, wherein the guiding portion of the valve member has a solid conical shape.

8. The blood collection needle according to claim 1, wherein the guiding portion includes a hollow column shape and communicates with the opening of the bowl portion through the bottom of the bowl portion.

9. The blood collection needle according to claim 1, wherein the guiding portion includes a hollow conical shape and communicates with the opening of the bowl portion through the bottom of the bowl portion.

10. The blood collection needle according to claim 1, wherein the hub includes a vent path for communicating the internal passage to an outer atmosphere, and an air permeable/blood impermeable filter fixed within the vent path in a liquid-tight manner.

11. The blood collection needle according to claim 2, further including a spring member which urges the valve member in a direction to close the internal passage, the spring member being disposed in the void of the hub.

12. The blood collection needle according to claim 11, wherein the spring member is clamped between the bowl portion of the valve member and a wall surface on the side of the needle tube for puncturing the rubber plug.

* * * * *